United States Patent [19]

Wallshein

[11] 3,988,832
[45] Nov. 2, 1976

[54] ORTHODONTIC ARCH WIRE

[76] Inventor: Melvin Wallshein, 8645 Bay Parkway, Brooklyn, N.Y. 11214

[22] Filed: Dec. 23, 1974

[21] Appl. No.: 535,687

Related U.S. Application Data

[63] Continuation-in-part of Ser. No. 300,444, Oct. 10, 1972, Pat. No. 3,861,042, and a continuation-in-part of Ser. No. 476,479, June 5, 1974, Pat. No. 3,878,609.

[52] U.S. Cl. .............................................. 32/14 A
[51] Int. Cl.² ........................................ A61C 7/00
[58] Field of Search ................................ 32/14 A

[56] References Cited

UNITED STATES PATENTS

| | | | |
|---|---|---|---|
| 3,052,081 | 9/1962 | Wallshein | 32/14 A |
| 3,250,003 | 5/1966 | Collito | 32/14 A |
| 3,593,421 | 11/1967 | Brader | 32/14 A |
| 3,838,515 | 10/1974 | Paugh | 32/14 A |

OTHER PUBLICATIONS

Canning, Post Office Box 869, Denver Colo.

ORMCO, 1332 S. Lone Hill Rd., Glendora, Calif., p. 40 "Coil Springs."

Primary Examiner—Robert Peshock
Attorney, Agent, or Firm—Flynn & Frishauf

[57] ABSTRACT

An orthodontic arch wire and a method of forming the same are disclosed, the method including the steps of coiling a single flexible metallic strand to form a tightly wound helix normally having an array of successively abutting and substantially parallel turns. The helix is made from a material sufficiently flexible to permit bending of the arch wire by selectively and at least partially separating adjacent turns of the helix. According to one presently preferred embodiment, the adjacent turns each lie in a respective plane extending substantially transversely to the longitudinal axis of the helix.

26 Claims, 10 Drawing Figures

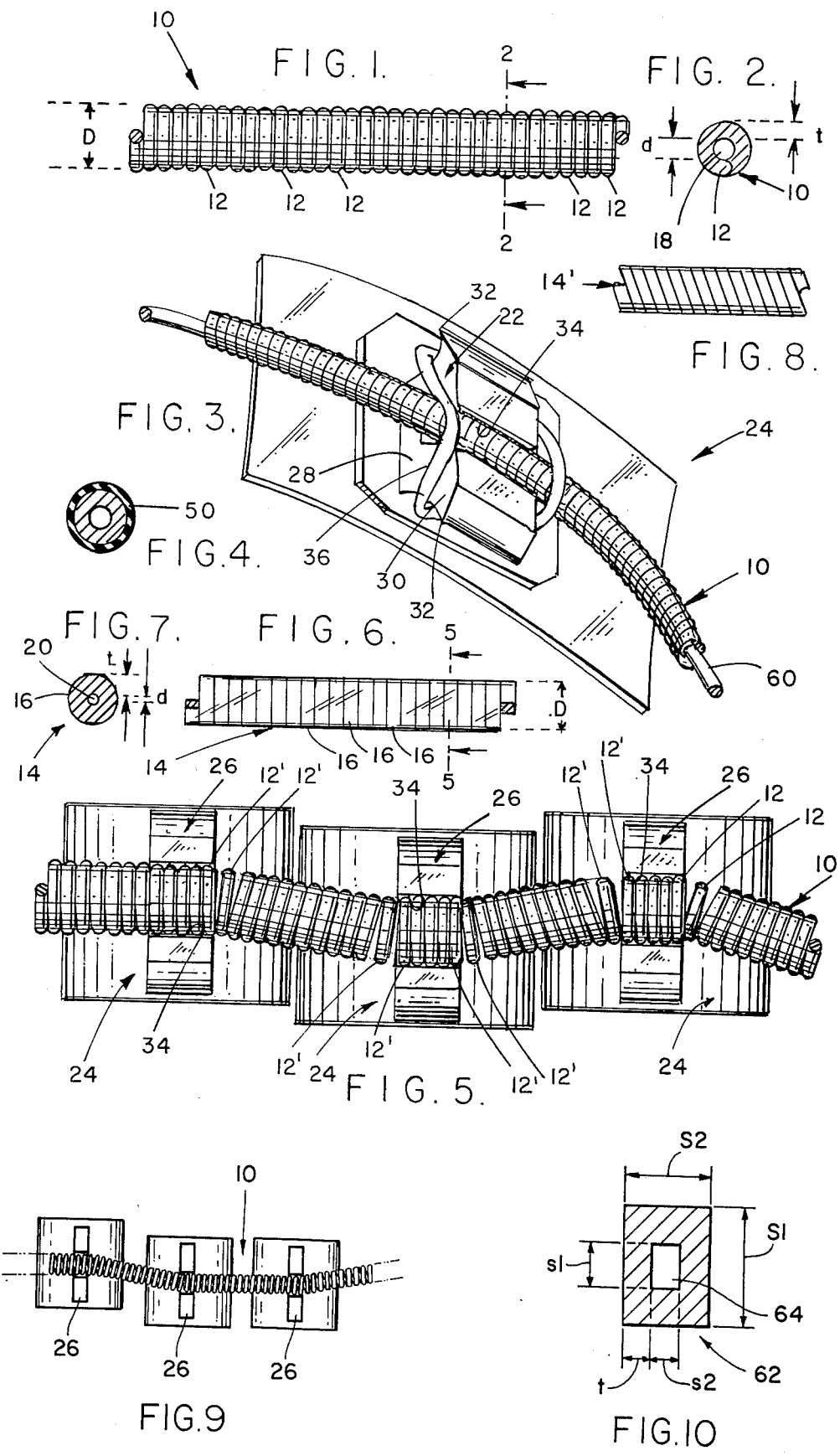

ORTHODONTIC ARCH WIRE

This is a Continuation-In-Part of U.S. Pat. application Ser. Nos. 300,444, filed Oct. 10, 1972, now U.S. Pat. No. 3,861,042 issued Jan. 21, 1975; and 476,479 filed June 5, 1974, now U.S. Pat. No. 3,878,609 issued Apr. 22, 1975.

The present invention generally relates to orthodontic arch wires, and more particularly to an arch wire constituted of a single metallic strand in the form of a tightly wound helix.

The following definitions apply to the specification and claims. "Stiffness" is the resistance of a material to bending or deformation. "Flexibility" is the ability of a material to bending or deformation. "Plastic deformation" is a permanent change in the shape of a material. Once "plastic deformation" takes place, the removal of forces which caused the change in shape does not result in a return of the material to its original shape. The "elastic limit" of a material is the maximum load or deformation which can be applied to a material before plastic or permanent deformation takes place. "Resiliency" is the tendency of a flexed material to spring back to its original configuration on the removal of the flexing forces. "Working Range" is the maximum deformation which can be sustained by a material without exceeding the elastic limit and becoming permanently deformed with loss of resiliency.

Orthodontic procedures usually require the placement of a tooth band and bracket upon respective maloccluded teeth and the employment of an arch wire for interconnecting the bands or brackets relative to one another so that a force is transmitted from one band to the next and thereby to the teeth upon which the bands are mounted. Today, the orthodontist is offered a wide variety of arch wires. The known arch wires vary both in size and material. An ideal arch wire must be flexible, but must have sufficient stiffness or body over long lengths so that it can serve as a relatively fixed anchoring or reference point to which other orthodontic devices are connected. The flexibility, of course, is required so that the arch wire can be bent into the shape of an arch in the mouth. It is also desirable that the arch wire have a resiliency and sufficient range over short and long lengths in order to permit the application of local biasing forces to the teeth. Most wires do have the quality of resiliency over limited ranges of bending or deformation — these wires becoming permanently deformed and losing all resiliency once the wire is bent beyond its elastic limit. In other words, these wires have a limited working range, as defined above.

The known arch wires do not provide the required combination of characteristics which an ideal arch wire should possess. Thus, while most known arch wires are flexible and provide the requisite stiffness over long lengths, these wires have a limited working range over short lengths. In order to apply local stresses to one or more teeth, it is frequently necessary to provide individual areas along the arch wire which have a high degree of resiliency. Since known arch wires with their limited working ranges cannot normally provide this high degree of springiness or resiliency by mere bending — the normal method of activating the restoring forces — it has been the common practice to make large loops from the arch wire. By making large loops, the arch wire is not drastically bent in a short length, but rather is curved over a longer length of the large loop. In this manner, the elastic limit of the wire is not exceeded at any one point and the wire retains its resiliency.

The solid wire, which is the most common type used, exhibits the requisite flexibility and stiffness over long lengths. However, a generally long length of the solid wire is required to obtain any meaningful amount of flexing without permanently deforming the wire. In a small space of approximately three milimeters, solid wire is practically rigid, does not have the requisite working range; and if the wire is bent in such a small space, it is permanently deformed and does not tend to spring back to its initial configuration.

In order to increase the working range of a wire in a small space, solid wires have been replaced in some instances by multiple-wire arrangements in which a plurality of thin wires are combined to provide an effective cross-sectional area which is substantially equal to the original cross-sectional area of the solid wire. The multiple arch wire is more flexible than the solid wire of comparable cross-section. The working range, however, of the multiple-wire arrangement is greater than the solid wire counterpart. The multiple-wire still has sufficient stiffness or body, although this is less than the solid wire. Despite the desirable increase in working range, the multiple arch wire has other disadvantages which have limited its use. For example, the ends of the multiple-wires have formed impaling or piercing devices upon the tissues in the mouth. The ends of the multiple arch wires spread out in time and impair the sensitive tissues in the mouth. Also, the thinner individual strands are relatively weak and subject to rupture. Generally, the strands do not rupture as a unit, but each strand ruptures under the pressure of the bite or something abrasive in the mouth. Thus, the multiple arch wire has a weakness which makes it unable to hold up to stresses in the mouth. To aggravate the problem, rupture of the individual strands causes the ruptured free ends to spread out in time and mutilated sensitive tissues of the mouth.

A further attempt in the evolution of arch wires to obtain the combined characteristics of flexibility, stiffness over long lengths, resiliency and an increased working range in short lengths has been the development of arch wires formed from multiple strands which are twisted together in the form of a rope. This twisted arch wire is more flexible than a corresponding solid arch wire of comparable cross-section since the flexibility of the twisted wire is related to the greater flexibility of the individual minor strands. Thus, although the overall cross-sectional areas of both the solid wire and the twisted wires may be approximately equal, the flexibility of the twisted arch wire is substantially greater than that of the solid wire. Over short lengths, however, the twisted wire has a greater working range than a solid wire and can be bent to a greater extent without being permanently deformed and loosing its resiliency. The twisted wire, being made from a plurality of thinner and weaker wires, as in the multiple-wire arrangement, has the same disadvantages as the latter. However, tightly wound multiple wires have had a lesser tendency to open up and fray than the above described multiple-wire arrangement.

Also, there is known in the prior art, a solid arch wire which includes a plurality of spaced helical convolutions which can be either openly or closely wound. However, the convolutions form only a relatively small portion of the overall arch wire length and are provided as coils spaced on a solid arch wire instead of being a coil forming the entire length of the arch wire as the basic configuration of the arch wire. With this known arch wire, in the case of the open convolutions, the required stiffness over long lengths is lost. The provision of spaced closed convolutions only along sections of the arch wire decreases the versatility at which bends may be made in the arch wire. Thus, the last described arch wire basically consists of a solid arch wire with spaced coils thereon.

The improvement of the present invention over that of U.S. Pat. application Ser. No. 300,444 is to provide an orthodontic arch wire which is wound substantially in accordance with the techniques disclosed in U.S. Pat. application Ser. No. 300,444, but wherein the turns of the arch wire have a common internal dimension more than two and no greater than three times the predetermined radial thickness of the strand from which the wire is formed. The strand is of a material sufficiently elastic to permit bending of the arch wire over a short length thereof by selectively and at least partially separating adjacent turns.

BRIEF DESCRIPTION OF THE DRAWINGS

FIG. 1 is a front view of the orthodontic arch wire pursuant to one embodiment in accordance with the present invention;

FIG. 2 is a cross-sectional view taken along the line 2—2 in FIG. 1;

FIG. 3 is an enlarged fragmented perspective view of an orthodontic bracket in association with the orthodontic arch wire pursuant to the embodiment illustrated in FIG. 1;

FIG. 4 is a view similar to that of FIG. 2, showing the addition of a plasticized coating on the exterior of the wire;

FIG. 5 is an enlarged front elevational view of adjacent orthodontic brackets as mounted on respective teeth (not shown) and, as associated with a common orthodontic arch wire pursuant to the embodiment illustrated in FIG. 1;

FIG. 6 is a view similar to that of FIG. 1 of an alternate embodiment of the present invention which uses a strand having a rectangular cross-section;

FIG. 7 is a cross-sectional view taken along the line 5—5 in FIG. 6;

FIG. 8 is a view similar to that of FIG. 6, showing an orthodontic construction of the second embodiment wherein the turns are inclined at a steeper angle with respect to the axis of the wire;

FIG. 9 illustrates the arch wire as a retraction device; and

FIG. 10 is a cross-sectional view, similar to FIG. 7, of a further embodiment of the present invention, wherein the arch wire is rectangular as is the lumen extending therethrough.

DETAILED DESCRIPTION OF THE PREFERRED EMBODIMENTS

Referring now to the drawings, and more particularly to FIGS. 1 and 2, the present invention may be characterized as relating to an orthodontic arch wire which is generally designated by the reference numeral 10. The arch wire 10 is elongated and defines an axis of symmetry which passes through the central region of the wire. The advantages of the present arch wire, which will be more fully described hereafter, are made possible by the specific construction of the arch wire. The arch wire is made from a single strand having a circular cross-section having a diameter t. The strand is configurated into a tightly wound helix having successively abutting looped turns 12 of generally circular cross-section. Each turn 12 of the helix defines a plane which is normally substantially parallel to the other respective planes defined by the other turns when the arch wire 10 extends along a straight line. According to one presently preferred embodiment, the parallel planes defined by the turns are substantially perpendicular to the axis of the arch wire — this being shown in FIG. 1.

The arch wire, as shown in FIGS. 1 and 2, is configurated into a helix and has looped turns 12 each with a common internal diameter d which is equal to or less than twice the diameter or thickness t of the individual strand from which the orthodontic arch wire 10 is made as measured in the radical direction of the helix. The outer dimension of the arch wire 10 is in the range of dimensions commonly used for arch wires — solid or otherwise. The orthodontic arch wire 10 is constituted of a single metallic strand, preferably stainless steel, which is relatively flexible in nature.

The internal dimension d is advantageously made as small as practical in order to provide the required stiffness of the wire over long lengths. The opening in each of the turns having the internal dimension d together form a passage or lumen through the arch wire 10. The passage is normally created during the formation of the helix. Thus, one way of manufacturing the arch wire in accordance with the present invention comprises the step of configurating a wire into a tightly wound helix about a mandrel 60 (shown in FIG. 3), which may or may not be left in the arch wire subsequent to the manufacture thereof. Slightly modified characteristics of the arch wire 10, which may be desirable in certain cases, may be obtained by leaving the mandrel 60 in the lumen of the arch wire.

Because of the tight abutting relationship of each of the looped turns 12 to each other, the resultant arch wire 10 is provided with an enhanced degree of stiffness — a degree of stiffness which is greater than that of an openly wound helix made from a similar strand. Thus, whereas an open helix or coil would have substantial flexibility over longer lengths of the arch wire, the subject arch wire 10 has a stiffness which almost equals that of a solid wire of equivalent cross-sectional area. This arises partly from the support which adjacent turns offer to one another. Of course, because of the looped configuration, the arch wire 10 is somewhat more flexible and less stiff than its solid wire counterpart over long lengths. The stiffness is also greatly enhanced by minimizing the diameter of the inner passage of the wire 10. Selecting the lumen or passage diameter to be a dimension at least two times, but not greater than three times the diameter of the coil strand provides an arch wire which still has the desired rigidity of an arch wire, and which also has sufficient flexibility to render it useful as a retraction arch. Such a construction eliminates the necessity to provide external appliances or specially configure the arch wire to exert forces. Thus, no loops, rubberbands, etc. are required.

More specifically, the arch wire having the lumen or passage diameter more than twice, but not more than three times the diameter of the coil strand provides the additional advantage in that the coil may be longitudinally pulled so as to extend same in the longitudinal direction thereof, thereby tending to separate the adjacent turns of the coil. It has been found that arch wires having this type of construction, with the abovedescribed constraints on the diameter of the passage and the diameter of the coil strand provide a wire which has all of the characteristics of the wire of my U.S. Pat. application Ser. No. 300,444, but additionally enables the wire to be used in an "expanded" state wherein it tends to spring back to the original shape shown in FIG. 1. As described above, such use is achieved by anchoring the wire at one point, and stressing it longitudinally at another point so as to tend to separate the adjacent turns thereof. Such an application is illustrated in FIG. 9 wherein the arch wire 10 is shown in its expanded state between two adjacent tooth brackets 26. The arch wire 10 of FIG. 9 tends to pull the tooth brackets 26 toward each other due to the spring-type retractive force of the helical arch wire. By providing the arch wire with a lumen or passage diameter which is more than two times the diameter of the coil strand, but which is no more than three times the diameter of the coil strand, the type of operation illustrated in FIG. 9 is advantageously achieved. Additionally, the arch wire of the present invention still retains substantially all of the advantageous characteristics described in my U.S. Pat. application Ser. No. 300,444.

FIGS. 1 – 8 in the present application are identical with those of my said prior applications and the description thereof appearing below is substantially identical with that appearing in said U.S. Pat. application Ser. No. 300,444.

Orthodontic procedures usually incorporate the utilization of an orthodontic bracket, shown in FIG. 3, generally denoted by the reference character 22. The bracket 22 is mounted on a band 24, only a fragment of the band being illustrated in FIG. 3. The band is generally annular-like and is configured to be tightly fitted and mounted upon a respective tooth (not shown). Brackets are sometimes directly mounted on a tooth by bonding the bracket to the tooth with cement. The bracket 22 has a base portion 28 and a flanged portion 30. The flanged portion 30 is provided with a pair of oppositely directed lips 32 which overlie in spaced relationship the base portion 28 of the bracket 22. Moreover, the bracket is provided with, between the opposite lips 32, a centrally disposed generally U-shaped wire guide-channel 34. An orthodontic arch wire, such as wire 10, is receivable into the guide-channel 34. A conventional ligature or fastener 36 is forced over the oppositely directed lips 32 in a conventional manner so as to be detachably associated with the flanged portion 30 to thereby tightly secure the orthodontic arch wire 10 within the guide channel 34.

Normally, a plurality of orthodontic brackets are mounted on respective teeth and, thereafter, are interconnected to one another through the intermediary of an orthodontic arch wire 10 in a manner generally examplified in FIG. 5. In FIG. 5, however, there is omitted from the illustration the fastener 36 illustrated in FIG. 3. The reason for omitting the fastener from FIG. 5 is to permit illustration of the manner by which the orthodontic arch wire 10 pursuant to the first described embodiment illustrated in FIGS. 1 and 2 permits "localized" control over the directional movement of a maloccluded tooth. When the arch wire 10 is appropriately mounted and constrained within the guide channel 34 of each of the orthodontic brackets 22, the arch wire may be longitudinally tightened so as to cause movement of the maloccluded teeth in directions generally longitudinally of the wire 10. The arch wire 10 pursuant to the present invention, when mounted within the appropriate guide channels 34 of each of the orthodontic brackets 22 respectively, may be flexed or bent slightly or significantly. At such time, the loop turns 12 originally abutting against one another prior to being mounted within the orthodontic brackets 22 will resiliently flex at localized positions on either side of the guide channel 34 of each of the brackets 22. Although slight bending is shown in FIG. 5, the wire 10 can be bent significantly without permanently being deformed and loosing its resiliency. Thus, the wire 10 provides an improved working range over that provided by solid wires. During this process, adjacent turns slightly or at least partially separate from one another in a manner illustrated in FIG. 5. Those turns which experience this partial separation, are generally designated by the reference character 12' in FIG. 5.

The slight separation of the originally abutting looped turns 12' of the arch wire 10 permits localized control over the vertical alignment of a particular tooth since the turns 12' as slightly separated from one another tend to elastically return to an abutting orientation thereby causing a maloccluded tooth to properly align itself vertically. The increased working range of the arch wire 10 insures that the arch wire retains its resiliency despite substantial flexing thereof.

Accordingly, the single metallic strand from which the orthodontic arch wire 10 is formed overcomes the disadvantages typically associated with single strands of solid wire which are not helically coiled in a manner pursurant to the present invention. With the conventional wires, as described in the BACKGROUND OF THE INVENTION, these do not provide the requisite working range over small lengths in the range of 2 to 4 millimeters. However, by imparting a tightly-wound helical configuration as above described, bending of the arch wire 10, is possible to a greater extent without permanently deforming the wire. It has been found that a wire having the above described helical construction provides increased flexibility as well as increased working range in small spaces — this being particularly suitable for orthodontic work.

The single strand coil pursuant to the present invention overcomes the deficiencies of multi-strand arch wires in several respects. Firstly, the subject arch wire 10 is usually more flexible than the multi-strand arch wire since the flexibility of the present arch wire is limited only by a single strand while in the multiple arch wire configurations the overall flexibility is a function of the combined flexibility of all of the individual strands. Additionally, the subject arch wire can be made to resist abrasive objects in the mouth better than the multi-strand arch wire by making the single strand in the present invention have a dimension greater than that of the individual strands in the multi-strand arch wire configuration without compromising working range over short lengths. Also, by making the single strand of the subject wire somewhat greater in cross-sectional area than the cross-sectional areas of the individual strands of the multi-strand arch wire, the danger of breakage and subsequent piercing and multilation of the sensitive tissues in the mouth are similarly decreased or eliminated. Further, the wire of the present invention can also serve as a retractive device.

Optionally, a soft coating 50 may be placed about the exterior of the arch wire 10 — this being illustrated in FIG. 4. Advantageously, the coating can be made from a plasticized material which can simultaneously serve to protect the tissues in the mouth from the wire as well as to prevent food particles from entering into the spaces in the wire where they may decay and present problems to the wearer of the arch. The coating 50, being plasticized and elastic, does not substantially effect the flexibility or working range of the arch wire 10.

Although the above embodiment was described in terms of a strand of circular cross-section which makes up the helix or arch wire, any other suitable cross-section of the strand and/or of the looped turns 12 may be utilized. Thus, the looped turns 12 have been shown to be circular, although oval or rectangular turns may also be utilized. In FIGS. 6 and 7, rectangular looped turns 16 are shown which similarly successively abut against each other — the turns being capable of being made from a strand of square or rectangular cross-section. In accordance with the present invention, the common internal dimension d is related to the thickness t of the strand as follows:

$$2t < d \leq 3t.$$

As before, the orthondontic arch wire 14 is constituted of a single preferably metallic strand such as stainless steel which is flexible in nature and coiled into a square coil such that each of the looped turns 16 of the wire 14 abuts against adjacent turns and are positioned in respective planes which are substantially parallel to one another. Also, each of the square turns 16 defines a plane which is substantially normal to the axis of the elongated arch wire 14. The square wire 14 functions in the same manner as does the arch wire 10 and exhibits similar properties over the long and short lengths as described above.

In connection with both the arch wires 10 and 14, the turns have up to now been described as defining planes which are substantially normal to the axis of the respective arch wires. A slight modification of both of these embodiments is shown in FIG. 8 wherein each of the turns, circular or rectangular, each define a plane which is oblique to the axis of the respective arch wires. This modification prevents the fastening wires 36 from entering between and separating the adjacent turns since these fastening wires are also generally in planes which are substantially normal to the axis of the arch wires.

It should be clear that in the embodiment illustrated in FIG. 9, the orthodontic brackets 26 may be located with respect to each other as shown in FIG. 5, in addition to the adjacent teeth being separated from one another. In this arrangement, the arch wire serves the function described with respect to FIG. 5, and additionally serves as a retraction arch as shown in FIG. 9 so as to provide a compound orthodontic effect. In FIG. 9, the separation of the adjacent turns of the arch wire is exaggerated for ease of illustration. In practice, the turns of the arch wire are only slightly separated when the wire is stretched to provide the retraction forces.

The arch wire may have a square or rectangular configuration or cross section instead of the cylindrical cross section shown, for example, in FIG. 1. The cross section of such a rectangular wire is shown in FIG. 10. The wire is designated by the reference numeral 62 and is formed from a strand having a thickness $t$. The wire 62 has common external dimensions designated by S1 and S2. A square lumen 64 extends through the arch wire 62 having internal common dimensions $s1$ and $s2$. It is pointed out that the wire 62 may be formed from a strand having either a circular or rectangular cross section. When a wire having a rectangular cross section is utilized, the wire is generally wound about one of its longer sides. This is true for both arch wires having rectangular as well as round turns and made from rectangular strands.

The arch wire having the rectangular outer shape of FIG. 10 may be fabricated by winding a wire (round or rectangular) to form a round lumen, and then passing the round arch wire through rollers or the like to compress or form the round arch wire into a wire having a generally rectangular outer shape. The lumen will also change its shape accordingly due to the compression of the rollers. Four rollers, adjacent ones being at right angles to each other, will provide sufficient forming forces. The arch wire fed to the rollers preferably has the relationship $d \leq 3t$, and most preferably has the relationship $2t < d \leq 3t$.

As described above, the largest wire receiving channels commonly found in edgewise-type brackets are dimensioned approximately 0.022 inches. When a rectangular arch wire 62 is formed, clearly, the outside dimensions thereof S1 and S2 can be made approximately equal to the maximum anticipated dimensions of the arch wire receiving channel. It is anticipated that rectangular arch wires having common outer dimensions no greater than approximately 0.025 inches by 0.032 inches are suitable for most commonly used brackets. This includes the Begg-type brackets whose wire receiving channels may be as large as 0.22 inches by 0.040 inches. Manufacturing techniques and tolerances may result in arch wires having slightly smaller or larger dimensions.

As described above, the use of square or rectangular strands and the formation of either cylindrical or rectangular arch wires is advantageous since it eliminates the notches or curved indentations between adjacent turns, as best shown in FIGS. 1 and 5. This permits free slidable movement of the arch wire through the channel without locking engagement with the ligatures 36.

An important feature of the present invention resides in that the arch wire having said relationship $$2t < d \leq 3t.$$

may be advantageously used with or without the mandrel 60 in place. With the mandrel 60 in place, the arch wire of the present invention, when used in the mode illustrated in FIG. 5, gives performance of the arch wire described and claimed in my prior U.S. Pat. application Ser. No. 476,479, and in addition to having the stiffness of said prior arch wire, the arch wire of the present invention may be elongated relative to the mandrel so as to provide retraction effects in addition to the effects illustrated in FIG. 5 so as to provide said compound orthodontic correction forces. Even when used without the mandrel 60 in place, the arch wire having the relationships in accordance with the present invention provides sufficient stiffness for use in many or most applications, while also providing the retraction forces as illustrated in FIG. 9. Thus, a single arch wire can be used with or without a mandrel inserted therein so as to provide effects which were heretofore obtainable only when using diverse types of arch wires.

The arch wire of the present invention is a multipurpose arch wire which may take the place of numerous orthodontic appliances and numerous types of arch wires which have heretofore been used in the orthodontic field.

The entire contents of my said prior application Ser. Nos. 300,444 and 476,479 are incorporated herein by reference.

I claim:

1. An orthodontic arch wire adapted to be connected to an orthodontic bracket mounted on a malloccluded tooth, the arch wire comprising a single coiled strand in the form of a tightly wound helix normally having an array of successively abutting and substantially parallel substantially circular turns, said strand having a substantially cylindrical lumen extending therethrough, said strand when formed into said turns having a predetermined radial thickness, said turns having a common internal dimension of said lumen greater than twice said predetermined radial thickness of said strand but no more than three times said predetermined radial thickness of said strand, and having a common outer dimension no greater than approximately 0.025 inches, said helix being made from a wire material sufficiently elastic to permit bending of the arch wire over a short length thereof by selectively and at least partially separating adjacent turns, to permit stretching thereof to separate adjacent turns, and to provide sufficient stiffness over a long length to provide adequate anchoring characteristics for orthodontic devices attached thereto.

2. An orthodontic arch wire as defined in claim 1, wherein the arch wire normally defines an axis and wherein each of the turns lies in a respective plane substantially normally to the axis.

3. An orthodontic arch wire as defined in claim 1, wherein said wire material has a generally rectangular cross-section.

4. An orthodontic arch wire as defined in claim 1, wherein said wire material has a substantially circular cross-section.

5. An orthodontic arch wire as defined in claim 1, wherein said helix defines an elongate axial passage through said turns, and further comprising a flexible mandrel extending through said passage.

6. An orthodontic arch wire as defined in claim 1, further comprising an external flexible coating extending along and covering said helix.

7. An orthodontic arch wire as defined in claim 6, wherein said coating is made of an elastomeric material.

8. An orthodontic arch wire as defined in claim 1, in combination with an orthodontic bracket having a guide channel for receiving said coiled strand, further including securing means detachably associated with said bracket for confining said coiled strand in said guide channel.

9. An orthodontic arch wire as defined in claim 5, wherein said mandrel is made of a wire material.

10. An orthodontic arch wire adapted to be connected to an orthodontic bracket mounted on a maloccluded tooth, the arch wire comprising a single coiled strand in the form of a tightly wound helix normally having an array of successively abutting and substantially parallel, substantially rectangular turns, said strand having a substantially rectangular lumen extending therethrough, said strand when formed into said turns having a predetermined thickness, said turns having a common internal dimension of said lumen greater than twice said predetermined thickness of said strand but no more than three times said predetermined radial thickness of said strand, and having a common outer dimensions no greater than approximately 0.025 inches by 0.032 inches, said helix being made from a wire material sufficiently elastic to permit bending of the arch wire over a short length thereby by selectively and at least partially separating adjacent turns, to permit stretching thereof to separate adjacent turns, and to provide sufficient stiffness over a long length to provide adequate anchoring characteristics for orthodontic devices attached thereto.

11. An orthodontic arch wire as defined in claim 10, wherein the arch wire normally defines an axis wherein each of the turns lies in a respective plane substantially normal to the axis.

12. An orthodontic arch wire as defined in claim 10, wherein said wire material has a generally rectangular cross-section.

13. An orthodontic arch wire as defined in claim 10, wherein said wire material has a substantially circular cross-section.

14. An orthodontic arch wire as defined in claim 10, wherein said helix defines an elongate axial passage through said turns, and further comprising a flexible mandrel extending through said passage.

15. An orthodontic arch wire as defined in claim 10, further comprising an external flexible coating extending along and covering said helix.

16. An orthodontic arch wire as defined in claim 15, wherein said coating is made of an elastomeric material.

17. An orthodontic arch wire as defined in claim 10, in combination with an orthodontic bracket having a guide channel for receiving said coiled strand, further including securing means detachably associated with said bracket for confining said coil to strand in said guide channel.

18. An orthodontic arch wire as defined in claim 14, wherein said flexible mandrel is a wire mandrel.

19. An orthodontic arch wire comprising a single coiled strand in the form of a tightly wound helix having a lumen extending therethrough and normally having an array of successively substantially abutting and substantially parallel turns, said strand when formed into said turns having a predetermined radial thickness and said turns having a common internal dimension of said lumen which is more than twice said predetermined radial thickness of said strand, but not more than three times said predetermined radial thickness of said strand, and having a common outer dimension no greater than approximately 0.025 inches, said helix being made from a wire material sufficiently elastic to permit bending of the arch wire by selectively and at least partially separating adjacent turns, and to permit longitudinal separation of adjacent turns.

20. An orthodontic arch wire as defined in claim 19 wherein said helix defines an elongate axial passage through said turns, and further comprising a flexible mandrel extending through said passage.

21. An orthodontic arch wire as defined in claim 20, wherein said mandrel is made of a wire material.

22. A method of applying an orthodontic arch wire to an orthodontic bracket on a tooth, said method comprising the steps of coiling a single flexible wire strand into a helix having a lumen extending therethrough and forming an array of successively substantially abutting, substantially parallel turns, said strand when formed into said turns having a predetermined radial thickness and said turns having a common internal dimension of said lumen more than twice said predetermined radial thickness of said strand but not more than three times said predetermined radial thickness of said strand, and having a common outer dimension no greater than approximately 0.025 inches; securing said coiled strand to said orthodontic bracket; applying a force to said coiled strand such that looped-turns adjacent said orthodontic bracket are at least partially moved out of contact with each other; and securing the coiled strand to said orthodontic bracket.

23. The method according to claim 22 comprising bending the coiled strand where desired such that a pair of looped-turns at each of the opposite ends of said orthodontic bracket are at least partially moved out of contact with each other.

24. The method according to claim 22 comprising coiling said single flexible wire strand around a flexible mandrel which is retained in said coiled strand.

25. The method according to claim 22 comprising extending said coiled strand in the longitudinal direction thereof such that looped-turns of said wire are at least partially moved out of contact with each other.

26. The method according to claim 23 further comprising extending the coiled strand at least over a portion of the length thereof in the axial direction of said portion.

* * * * *